United States Patent [19]
Herrick

[11] Patent Number: 4,781,187
[45] Date of Patent: Nov. 1, 1988

[54] METHOD AND IMPLANT FOR REFRACTIVE KERATOPLASTY

[76] Inventor: Robert S. Herrick, 4134 N. Rosemead Blvd., Rosemead, Calif. 90004

[21] Appl. No.: 897,865

[22] Filed: Aug. 19, 1986

[51] Int. Cl.$^4$ .............................................. A61B 17/32
[52] U.S. Cl. ....................................... 128/305; 623/4; 623/5
[58] Field of Search .................... 128/305, 303 R, 1 R; 623/4–6; 604/289–290, 294

[56] References Cited
U.S. PATENT DOCUMENTS
4,077,411   3/1978   Ward ................................... 128/305

FOREIGN PATENT DOCUMENTS
2095119   9/1982   United Kingdom ................... 623/5

*Primary Examiner*—John D. Yasko
*Assistant Examiner*—Gene B. Kartchner
*Attorney, Agent, or Firm*—Edward J. DaRin

[57] ABSTRACT

A method and implant for refractive keratoplasty or improved radial keratotomy. The improved radial keratotomy comprising making a plurality of radial corneal incisions in accordance with prior practices to correct the detected impaired vision. A piece of donor corneal tissue having a preselected geometric configuration and dimensions is inserted into keratotomy incisions and fixed in position by suturing. The corneal tissue implant may be rectangular or triangular in shape. When the implant is triangular in shape, it is inserted either base down or base up in accordance with the type of vision problem to be corrected.

7 Claims, 2 Drawing Sheets

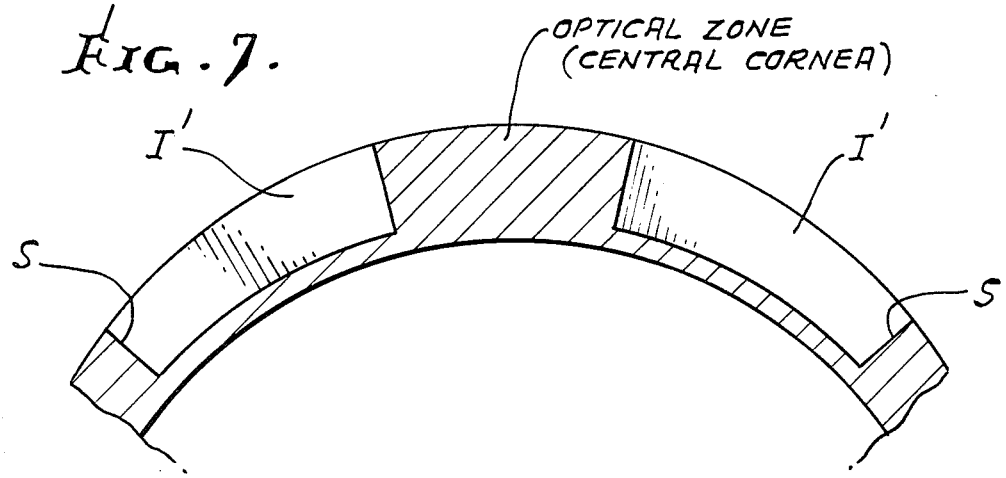
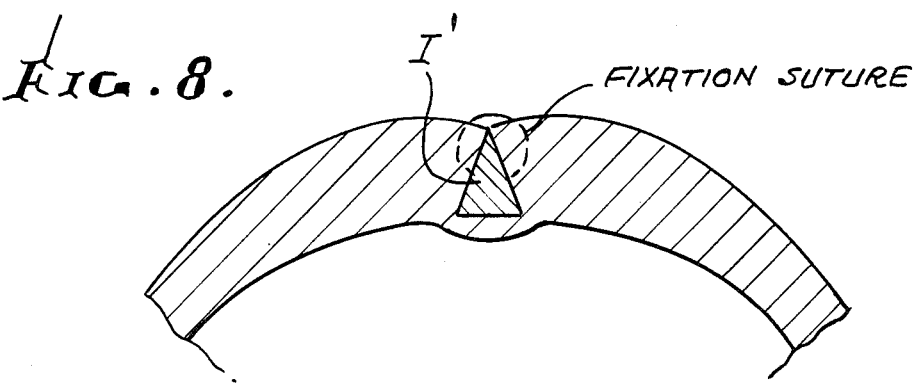
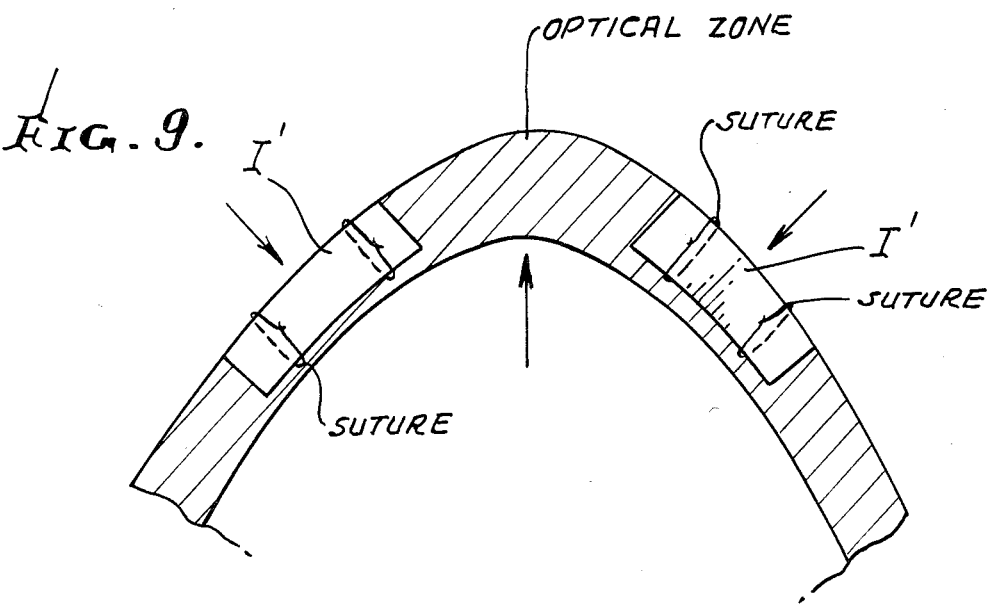

METHOD AND IMPLANT FOR REFRACTIVE KERATOPLASTY

FIELD OF INVENTION

This invention relates to an improved method for refractive keratoplasty and a corneal tissue implant.

BACKGROUND OF INVENTION

At the present time the correction of refractive errors in the human eye is being accomplished by radial keratotomy. Radial keratotomy consists of performing a plurality of corneal incisions for reshaping the cornea of the human eye and thereby the point of focus of light rays so that the eye will see normally once again (without glasses or contact lenses). These techniques of refractive surgery are discussed in detail in the text entitled "Refractive Surgery: A Text of Radial Keratotomy" by Sanders and Hofmann published by Slack Incorporated of Thorofare, N.J. 08086, copyright 1985.

It has been found that in performing the radial keratotomy that there are a number of undesirable factors resulting from such refractive surgery. These undesirable factors include glare, fluctuating vision, regression of correction, and overcorrections. Original astigmatism may be persistent or astigmatism is induced as a result of the surgery. It has also been found to have limited correction capabilities in cases of markedly high myopia. In addition, excessive scarring due to the wound gape and epithelial ingrowth, along with corneal weakening and an unstable cornea with lid blink has resulted. Accordingly, there is present need for eliminating or minimizing these undesirable factors or side effects resulting from present day radial keratotomy procedures.

SUMMARY OF INVENTION

The present invention provides an improved method of radial keratotomy through the placement of thin pieces of preselected geometric shapes, of donor cornea tissue in the gaping defect left by the incisions produced during the radial keratotomy. This unique method results in a number of advantages above and beyond the present day radial keratotomy surgery itself, namely, that it strengthens the cornea and encourages healing by primary intention instead of tertiary intention, thereby leaving the cornea with more than 5 to 10 percent of the corneal lamellae in tact for its strength. This improved procedure stabilizes the cornea and makes it more stable with lid blink. It also minimizes/eliminates glare since each incision provides more correction and thereby allows use of a larger central optical zone. The improved procedure requires fewer incisions, a minimum of two, for hyperopia and myopia and therefore more corrections are possible with fewer incisions because of the greater effect with each incision. Astigmatism alone might be corrected with as little as a single incision. It also minimizes refractive regression by stabilizing the cornea in a more permanent altered shape. The residual astigmatism, i.e., that existing prior to the radial keratotomy, may be altered by making one or more additional radial incisions with the corneal implant of the present invention. The induced astigmatism may be altered by either one or more additional radial incisions with a corneal implant or by removal or replacement with a thinner corneal implant and resuturing the wound when an overcorrection has been detected. Since there is no corneal gape, scarring is minimized, as well as the chance for secondary corneal ulcer. The gaping cracks in the cornea no longer exist, and therefore the location for bacteria to later lodge is eliminated or minimized. Stable vision would be obtained by an individual much earlier in time. Degrees of correction could be varied by variation in the widths of the corneal implants or the number of incisions and implants that may be utilized. There is less chance of perforation since the entire procedure would be in the thicker, mid-peripheral/peripheral corneal tissue due to the larger optical zone. Pachymetry is less critical in that standard 0.5 millimeter incisions can be used. Over-corrections could be altered in that the correction could be minimized by removing a corneal implant or replacing with a further corneal implant and immediately resuturing.

From an implant standpoint, the present invention comprises a corneal implant of donor corneal tissue shaped to a preselected geometric shape to be positioned into mid-peripheral radial keratotomy incisions for reshaping the central portion of a human cornea secondarily for correcting the impaired vision of a human eye. The selected geometric shape may be either triangular or rectangular, for example, and oriented with respect to the incision in accordance with the detected condition of impaired vision of the human eye to return the eye to normal vision.

From the standpoint of an improved method of radial keratotomy, the steps include producing a preselected number of radial keratotomy incisions in the cornea of a human eye, inserting a thin piece of donor corneal tissue into a preselected number of said corneal incisions and then fixing the thin pieces in position in the incisions. The thin pieces of corneal tissue are shaped to have a preselected geometric configuration in accordance with the desired correction needed in the refractive properties of the cornea. For the correction of myopia the geometric configuration may be either rectangular or triangular, and if the triangular shape is selected, the implant is inserted base out. If hyperopia is the vision problem, a triangular implant must be used and is inserted into the incision, base downwardly.

BRIEF DESCRIPTION OF THE DRAWINGS

These and other features of the present invention may be more fully appreciated when considered in light of the following specification and drawings, in which:

FIG. 7 is a diagrammatic representation of a portion of the central cornea or the optical zone of the human eye, illustrating the incisions having the implant therein for the purposes of correcting hyperopia;

FIG. 8 is a diagrammatic cross-section through the implant of FIG. 7, illustrating the orientation of a triangular shaped implant inserted with its base down in the incision; and FIG. 9 is a diagrammatic representation of the effects of the triangular shaped implant of FIGS. 7 and 8 on the curvature of the cornea with the forces illustrated indicated by the direction of the arrowheads for correcting for hyperopia.

DETAILED DESCRIPTION OF THE PREFERRED EMBODIMENTS

Figure 1:
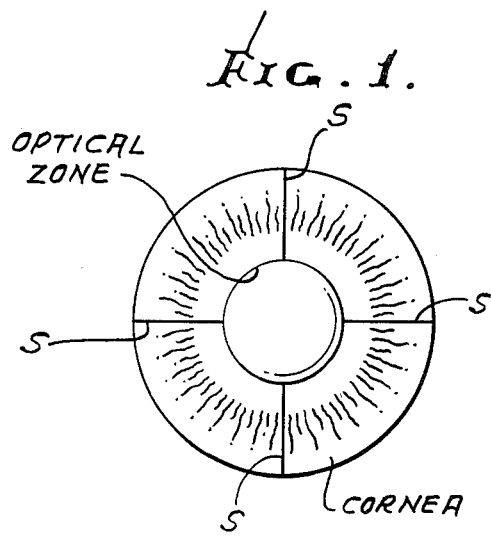
FIG. 1 is a diagrammatic view of the cornea of the human eye, illustrating four radial keratotomy incisions at spaced points in the cornea, as would normally be practiced in refractive surgery.
Figure 2:
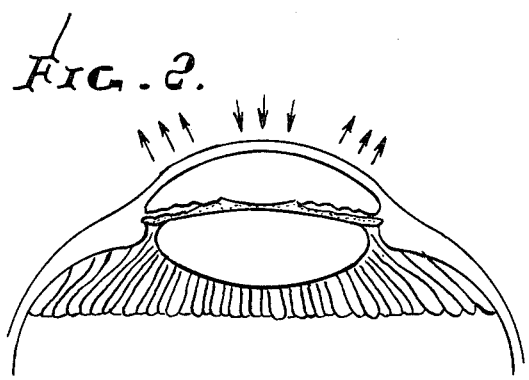
FIG. 2 is a diagrammatic view of the human eye, illustrating the forces shaping the cornea during normal radial keratotomy, the forces being indicated by the direction of the arrowheads.

Now referring to the drawings, the improved method of refractive keratoplasty and the implant of the present invention will be described in detail. Referring initially to FIGS. 1 and 2, wherein the diagrammatic representation of the cornea of the human eye is illustrated, it will be noted that FIG. 1 illustrates the central optical zone of the human cornea surrounded by the peripheral cornea. The surgical incisions are identified in FIG. 1 by the letters S, which are shown at four spaced positions thereon. The incisions S are illustrated as being 90° apart and being arranged at 12 o'clock, 3 o'clock, 6 o'clock, and 9 o'clock. The number of incisions S and their locations, of course, can be varied in accordance with the detected impaired condition of the human eye to modify the shape of the cornea in accordance with the detected impaired vision, such as astigmatism or myopia, as is well-known. The forces shaping the cornea during such radial keratotomy are illustrated in FIG. 2 and identified by the arrowheads which indicate the peripheral steepening of the cornea with the central flattening thereof.

Figure 3:
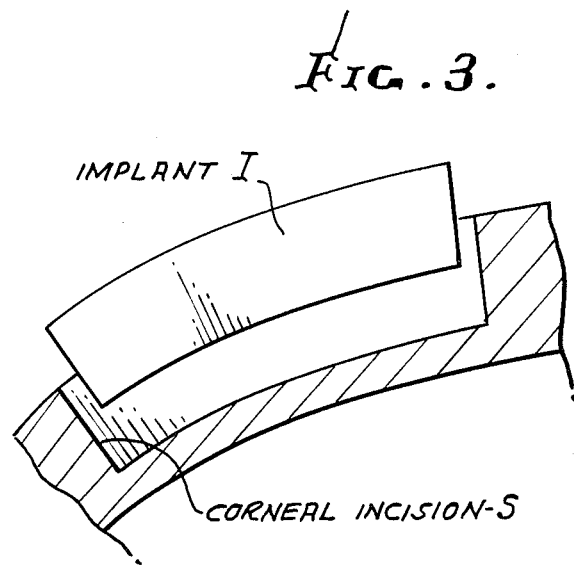
FIG. 3 is a diagrammatic representation of a corneal incision, illustrating the implant of the present invention partially inserted therein.
Figure 4:
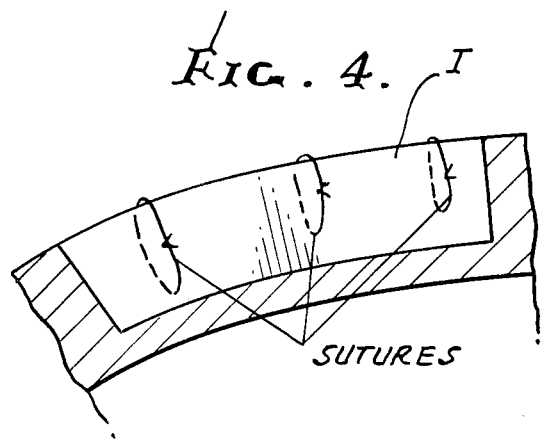
FIG. 4 is a diagrammatic representation of the implant of FIG. 2 illustrated in the proper relationship with the radial incision and showing the location of the sutures thereon;.
Figure 5:
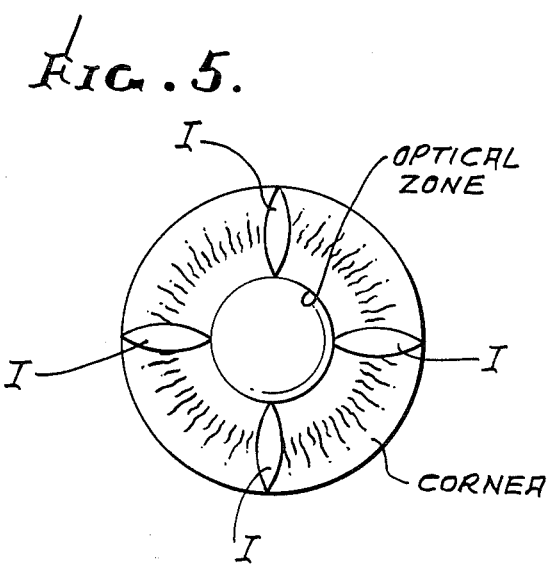
FIG. 5 is the diagrammatic representation of the cornea, as illustrated in FIG. 1, but with the implants in position for correcting for myopia.
Figure 6:
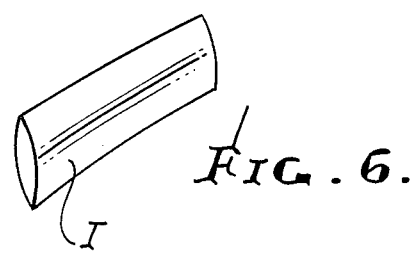
FIG. 6 is a detached diagrammatic view of the implant, as illustrated in FIGS. 3-5.

Now referring to FIGS. 3-6, the improved procedure for correcting for astigmatism or a degree of myopia will be described in accordance with the teachings of the present invention. The present invention takes advantage of the radial incisions S that are normally produced by the conventional radial keratotomy techniques by inserting a thin piece of donor corneal tissue, preferably of preselected standard dimensions and geometric shape for insertion into the incisions. The donor corneal tissue is commercially available and to form the implants I of the present invention is shaped either by hand or by laser. For the correction of myopia, for example, it is desired to have the cornea bulge outwardly so the implant I should have either a triangular configuration or a rectangular configuration. These implants typically may have dimensions that have been standardized on the order of a length of 3.5 to 4.0 millimeters, a width of 0.5 millimeters, and a thickness on the order of 0.1 to 0.3 millimeters. The detached view of such an implant I is illustrated in FIG. 6, wherein it has a generally rectangular configuration. The implant I is illustrated in FIG. 3 as being partially inserted into a radial keratotomy incision S. In FIG. 4 the implant I is shown in place within the incision and with a plurality of sutures secured thereto for fixing the implant I in place. The present invention recognizes that the incisions S resulting from the conventional radial keratotomy leave a gaping defect, and this gaping defect is utilized for positioning the implants I therein. After the implant I is positioned in the radial keratotomy incision, it is positioned by two or three interrupted 10-0 or 11-0 nylon sutures placed at right angles to the implant I through both the recipient and donor tissue, or the normal tissue of the human eye and the implant I. The sutures are placed at approximately half the corneal depth. During this procedure the corneal implant I would be held down at an appropriate depth while placing the sutures thereon. It will also be recognized that inaccurately placed sutures can be removed and replaced. The implants I can be depressed lightly below the surface curve of the cornea to compensate for any tendency to drift upwardly after the surgical procedures are completed. The regrowing corneal epithelium tends to compensate for any irregularity.

With sharp line near retinoscopy, the degree of correction obtained by this novel procedure could be determined in the late phase of the procedure, and minor modifications carried out. This would permit refinement of the overall procedure of the present invention. When the procedure is completed, the corneal tissue and curve is quite stable and undergoes minimal change with healing. The properly positioned implant I is illustrated in FIG. 5 in a diagrammatic fashion from the topside thereof. It will be noted that the implant of FIG. 6 is illustrated in FIG. 5 in its four radial positions in the patient's cornea, viewing the cornea from the top side (as in FIG. 1). Although a substantially rectangular configuration is utilized, a triangular implant I may be used for the same purpose. When a triangular implant is selected, it is mounted into the radial keratotomy incision S with the base out or with the apex of the triangle slipped into the radial incision first to assume the general configuration illustrated in FIG. 5.

Now referring to FIGS. 7-9, the improved procedures of the present invention for the correction of hyperopia will now be examined. For this type of surgical correction, the corneal implant I should be of a triangular configuration and is inserted into the radial keratotomy incision with the base of the triangle inserted first or inwardly. The dimensions of the triangular implant for the correction of hyperopia must also fit precisely within the radial keratotomy incision. After the necessary appropriate radial keratotomy incisions are performed, then, the triangular shaped corneal implant I' is inserted into the incisions with the base down in a manner indicated diagrammatically in FIG. 8. The placing of the implants I' in such an incision results in steepening of the central corneal curve secondary to the flattening effect on the mid-peripheral corneal curve by the base down corneal wedge implants I'; see FIG. 9. The results of this procedure can be monitored by the sharp line near retinoscopy. The triangular implant I' is fixed by sutures as described hereinabove. The amount of correction can be varied by the number of incisions and the width of the base for the triangular implant I'. The triangular implant I' is illustrated in FIG. 8 in a diagrammatic cross-section through the implant I', illustrating the position of the implant I' and the fixation suture.

In the event of the progression to hyperopia as a result of previously performed conventional radial keratotomy, as contrasted with naturally occurring hyperopia discussed hereinabove, this defect in vision can also be corrected by the techniques of the present invention. For this type of surgery two to four or more of the previously performed radial incisions are selected and marked. It should be noted that minor corrections require only two such incisions. The surface epithelium is removed in the areas of the selected incisions. The radial incisions are opened up with a smooth flat instrument, such as an iris spatula. The incisions are stroked with the spatula to remove as much ingrown epithelium as possible. The triangular shaped implant I' is then inserted base inward into the open incision S. The nylon sutures are placed at right angles through the recipient tissue and the implant to reapproximate the recipient corneal tissue at the surface of the radial incision as discussed hereinabove. When the triangular shaped implant I' is so positioned within the incision with the base downwardly (inwardly), it forces the recipient mid-peripheral cornea inwardly toward the anterior chamber, generating a secondary force of the central cornea outward away from the anterior chamber. This results in steepening of the curve of the central cornea, thus correcting for the hyperopia.

It should now be noted that the present invention by the use of the corneal implants of preselected standard dimensions and geometric configuration, the procedures using the radial corneal incisions are made more effective, more predictable and more stable while leaving the cornea in a stronger state. The improved procedure also allows for some adjustment of the results thereof, and can be more safely performed than the prior art procedures.

What is claimed is:

1. A method of radial keratotomy including the steps of producing a preselected number of radial keratotomy incisions in the cornea of a human eye for correcting impaired vision, providing a thin piece of donor corneal tissue of a preselected geometric configuration selected in accordance with the desired correction in refractive properties of the cornea to restore substantially normal vision and sized for insertion into said radial keratotomy incisions, inserting a thin piece of donor corneal tissue into a preselected number of said corneal incisions, in a preselected orientation in accordance with the desired correction in refractive properties, and fixing the thin pieces in position in said corneal incisions.

2. A method of radial keratotomy as defined in claim 1 wherein said thin piece of donor corneal tissue is shaped to be of a generally triangular configuration and is inserted into the incision, base down.

3. A method of radial keratotomy as defined in claim 1 wherein said thin piece of donor corneal tissue is shaped to be of a generally triangular configuration and is inserted into the incision, base out.

4. A method of radial keratotomy as defined in claim 2 wherein said thin piece of donor corneal tissue is shaped to be of a generally rectangular configuration.

5. A method of radial keratotomy as defined in claim 1 or 2 wherein said step of fixing said thin pieces of corneal tissue comprises suturing said thin pieces of corneal tissue to the human eye tissue.

6. A method of radial keratotomy as defined in claim 1 wherein said step of fixing said thin pieces of corneal tissue comprises suturing said thin pieces of corneal tissue to the human eye tissue at a plurality of spaced locations at approximately right angles to said pieces.

7. A method of radial keratotomy as defined in claim 6 wherein the step of suturing comprises suturing nylon sutures at approximately half the corneal depth.

* * * * *

UNITED STATES PATENT AND TRADEMARK OFFICE
CERTIFICATE OF CORRECTION

PATENT NO. : 4,781,187
DATED : November 1, 1988
INVENTOR(S) : Robert S. Herrick

It is certified that error appears in the above-identified patent and that said Letters Patent is hereby corrected as shown below:

Column 6, line 17, in Claim 4, "2" should be -- 1 --.

Column 6, line 21, in Claim 5, cancel "or 2".

Signed and Sealed this

Twenty-fifth Day of April, 1989

Attest:

DONALD J. QUIGG

*Attesting Officer*   *Commissioner of Patents and Trademarks*